United States Patent [19]
Akhavan-Tafti

[11] Patent Number: 6,045,991
[45] Date of Patent: Apr. 4, 2000

[54] COMPOSITIONS AND METHODS FOR GENERATING RED CHEMILUMINESCENCE

[75] Inventor: Hashem Akhavan-Tafti, Howell, Mich.

[73] Assignee: Lumigen, Inc., Southfield, Mich.

[21] Appl. No.: 09/304,000

[22] Filed: May 3, 1999

Related U.S. Application Data

[63] Continuation-in-part of application No. 08/894,143, filed as application No. PCT/US97/00015, Jan. 15, 1997, which is a continuation-in-part of application No. 08/585,090, Jan. 16, 1996, abandoned, and application No. 08/683,927, Jul. 19, 1996, abandoned.

[51] Int. Cl.⁷ ............... C12Q 1/00; C09K 11/06; C07D 277/62
[52] U.S. Cl. ............ 435/4; 252/301.24; 252/700; 548/157; 435/6; 435/7.1; 435/7.9; 435/18; 435/21; 435/28
[58] Field of Search ................ 435/4, 6, 7.1, 7.9, 435/8, 18, 21, 28; 252/301.24, 700; 548/157

[56] References Cited

U.S. PATENT DOCUMENTS 5,712,106  1/1998  Herrmann et al. ............... 435/8

*Primary Examiner*—John Kight
*Assistant Examiner*—Charanjit S. Aulakh
*Attorney, Agent, or Firm*—Richard S. Handley

[57] ABSTRACT

Compounds which generate red chemiluminescence on reaction with a phosphatase enzyme are provided as well as intermediates useful for their preparation. The chemiluminescent compounds comprise a luciferin ring system and an exocyclic enol phosphate group where the position on the luciferin ring system adjacent to the double bond is disubstituted. The chemiluminescent compounds are useful alone or within compositions containing a cationic aromatic compound in methods for producing chemiluminescence. The chemiluminescent reactions can be applied in assays for phosphatase enzymes and in assays employing enzyme-labeled specific binding pairs.

26 Claims, 7 Drawing Sheets

Reagent A 5000  1000  180  30  5 pg of ß-gal

Reagent B 5000  1000  180  30  5

PVDF

Reagent A 5000  1000  180  30  5

Reagent B 5000  1000  180  30  5

Nitrocellulose

COMPOSITIONS AND METHODS FOR GENERATING RED CHEMILUMINESCENCE

CROSS REFERENCE TO RELATED APPLICATION

This application is a continuation-in-part of applicant's U.S. application Ser. No. 08/894,143 filed on Aug. 13, 1997 which was the National Stage of International Application No. US97/00015 filed on Jan. 15, 1997 which is a continuation-in-part of Ser. Nos. 08/585,090 filed on Jan. 16, 1996, abandoned, and 08/683,927 filed on Jul. 19, 1996, abandoned.

FIELD OF THE INVENTION

The present invention relates to chemiluminescent compounds and compositions which react with a phosphatase enzyme to generate red chemiluminescence. The invention further relates to methods of producing red chemiluminescence. The invention also relates to the use of these methods in an assay for detecting the enzyme or for detecting enzyme-labeled specific binding partners in immunoassays, nucleic acid probe assays and the like.

BACKGROUND OF THE INVENTION

Various means of detecting chemiluminescence are known and in commercial use. One of the most convenient means is a charge-coupled device (CCD) which is commonly incorporated into a camera (CCD camera). This type of device is rapidly becoming accepted in laboratories because it allows quantitative imaging of virtually any shape object or set of objects and because of the ease of computerized data storage and processing. A unique feature of CCDs is their superior sensitivity to red light. Unfortunately, chemiluminescent compounds which are currently available for qualitative and quantitative detection of enzymes are blue or green emitting. Detection sensitivity of CCDs is markedly inferior at these wavelengths. Accordingly, chemiluminescent compounds which produce light in the red region of the spectrum are required to take full advantage of CCD detection technology.

Alkaline phosphatase (AP) is frequently used as a marker or label in enzyme-linked assays for biological molecules and other analytes of interest such as drugs, hormones, steroids and cancer markers. Chemiluminescent detection of this enzyme offers a safe, convenient and sensitive means to provide a quantitative measure of the amount of enzyme in a sample or of the amount of an enzyme-labeled analyte or labeled specific binding partner for an analyte. No chemiluminescent enzyme substrate in commercial use generates red chemiluminescence. Substrates which are capable of producing red chemiluminescence would prove advantageous when used in conjunction with CCD detection. Such substrates would preferably produce red chemiluminescence with high efficiency and of an extended duration. Both of these goals are met by the compounds and compositions of the present invention.

Applicant's published PCT application WO97/26245 discloses chemiluminescent heterocyclic compounds which produce light upon reaction with a phosphatase. Possible heterocyclic ring fragments include a 2-(4-hydroxy-2-benzothiazolyl)-2-thiazolyl group (luciferyl group).

The light-producing compound occurring in various species of beetles, termed luciferin, are oxidized by a luciferase to produce bioluminescence in vivo ranging from green to orange. Red luminescence can be produced using the native luciferin and luciferase in vitro at pH<7 and by autoxidation of luciferin in DMSO or aqueous base (W. D. McElroy, H. H. Seliger, E. H. White, Photochem. Photobiol., 10, 153–170 (1969)). Synthetic analogs of luciferin such as 4,6-dihydroxyluciferin and 6-aminoluciferin have been reported to generate red bioluminescence on reaction with luciferase (E. H. White, H. Worther, J. Org. Chem. 31, 1484–1488 (1966); E. H. White, H. Worther, H. H. Seliger, W. D. McElroy, J. Am. Chem. Soc., 88, 2015–2019 (1966)). Another analog, 5,5-dimethylluciferin produces red chemiluminescence in oxygenated DMSO or in aqueous alkaline solution but does not produce bioluminescence with luciferase (T. A. Hopkins, H. H. Seliger, E. H. White, M. W. Cass, J. Am. Chem. Soc., 89, 7148 (1967)). It is important to note that none of the red-emitting bio- or chemiluminescent reactions indicated above have found commercial utility in enzyme-linked assays such as immunoassays and DNA probe assays.

SUMMARY OF THE INVENTION

It is an object of the present invention to provide compounds and compositions which react with a phosphatase enzyme to provide red chemiluminescence.

It is also an object of the present invention to provide compounds and compositions which react with a phosphatase enzyme to provide red chemiluminescence for detection of enzyme conjugates.

It is an object of the present invention to provide compounds and compositions which react with a phosphatase enzyme to provide red chemiluminescence of long duration.

It is also an object of the present invention to provide compounds and compositions which react with a phosphatase enzyme to provide red chemiluminescence for detection with charge-coupled devices (CCDs) including CCD cameras and luminometers.

It is an object of the present invention to provide compounds useful as intermediates in preparing chemiluminescent compounds.

DESCRIPTION OF THE PREFERRED EMBODIMENTS

Figure 1:
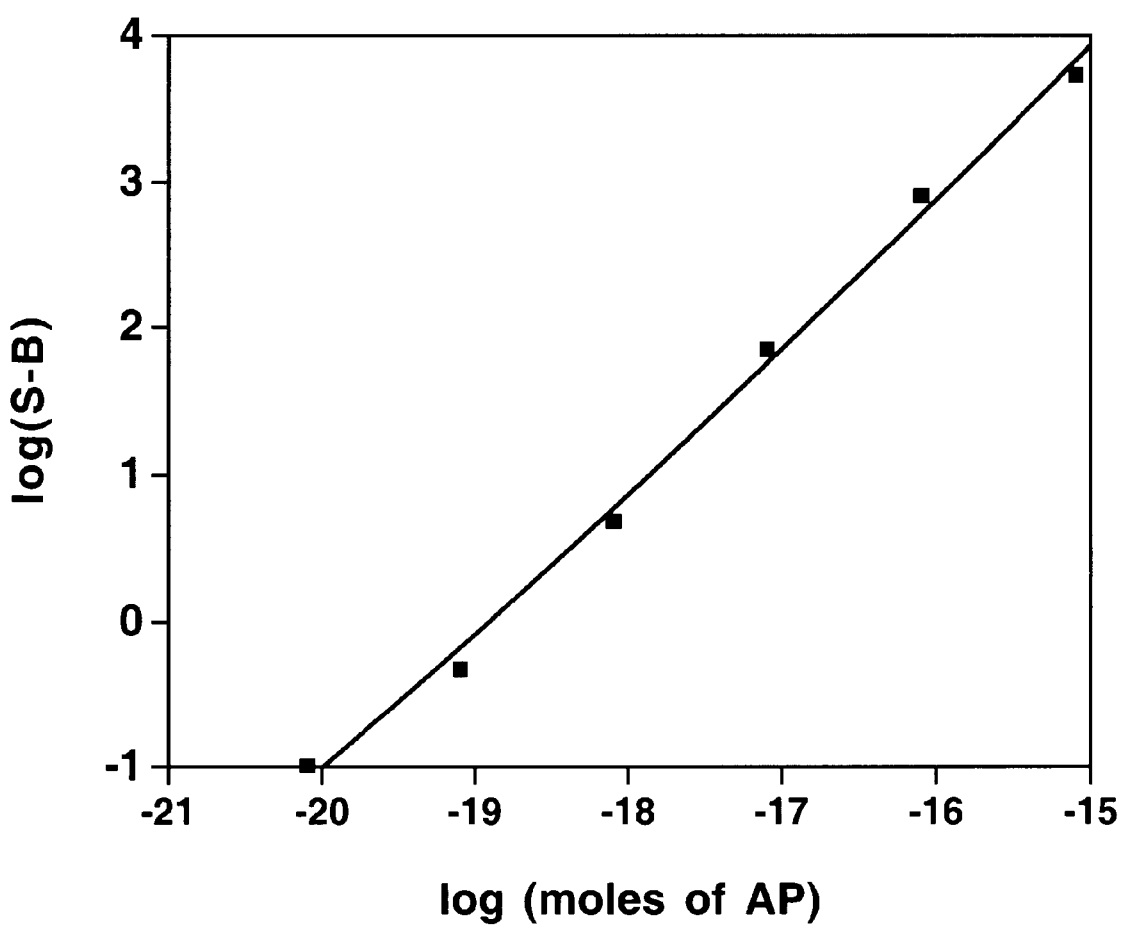
FIG. 1 is a graph relating the amount of AP to the chemiluminescence intensity emitted by a reagent of the present invention containing compound 4. Alkaline phosphatase detection sensitivity was assessed by combining 100 µL portions of a reagent composition comprising 0.1 M 221 buffer, pH 9.6, 0.33 mM compound 4, 0.1% Tween 20 and 0.1 mM lucigenin with 10 µL solutions of AP containing from $8 \times 10^{-16}$ to $8 \times 10^{-22}$ moles of enzyme. Light production at 25°C. was measured at 10 min. Data points are the average of triplicate analyses.

Definitions:

Alkyl—A branched, straight chain or cyclic hydrocarbon group containing from 1–20 carbons. Lower alkyl as used herein refers to those alkyl groups containing up to 8 carbons.

Alkenyl—A branched, straight chain or cyclic hydrocarbon group containing at least one C—C double bond and containing from 2–20 carbons. Lower alkenyl as used herein refers to those alkenyl groups containing up to 8 carbons.

Alkynyl—A branched or straight chain hydrocarbon group containing at least one C—C triple bond and containing from 2–20 carbons. Lower alkynyl as used herein refers to those alkynyl groups containing up to 8 carbons.

Analyte—A substance the presence or amount of which is to be measured in a sample by an assay. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody-DNA chimeras, antigens, haptens, proteins, lectins, avidin, streptavidin and biotin. Other exemplary analytes also include hydrolytic enzymes, inhibitors of hydrolytic enzymes and dihydroxyaromatic compounds.

Aryl—An aromatic ring-containing group containing 1 to 5 carbocyclic or heterocyclic aromatic rings, which can be substituted with 1 or more substituents other than H. Exemplary aryl groups include phenyl, naphthyl, pyridyl, quinolyl, furyl, thiophenyl and pyrrolyl.

Cationic center—A cationic center means a positively charged atom or group or a portion of a molecule with one or more sites of positive charge. Exemplary cationic centers include alkali metal ions, alkaline earth ions, ammonium, quaternary ammonium, and quaternary phosphonium ions, dicationic ammonium or phosphonium compounds and polymeric compounds with multiple cationic groups. Cationic centers are present in the number required by their valence.

Halogen—Fluorine, chlorine, bromine or iodine atoms.

Luminescent—capable of emitting light when excited to an electronic excited state. The light can be emitted either as fluorescence when decaying from a singlet excited state or as phosphorescence when decaying from a triplet excited state.

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include food samples and environmental samples such as soil or water.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

Substituted—Refers to the replacement of at least one hydrogen atom on a group by a non-hydrogen group. It should be noted that in references to substituted groups it is intended that multiple points of substitution can be present unless clearly indicated otherwise.

It has been discovered that compounds of formula I shown below react with phosphatase enzymes to generate red chemiluminescence of high intensity. Further, it has been found that compounds of formula I produce chemiluminescence of unexpectedly long duration. In the formula I:

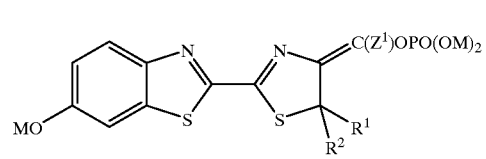

one of $Z^1$ and $Z^2$ is a group having the formula $OPO(OM)_2$ and the other is a group selected from $OR^3$ and $SR^3$, $R^3$ is selected from substituted or unsubstituted alkyl, substituted or unsubstituted aryl, and substituted or unsubstituted aralkyl groups, $R^1$ and $R^2$ are independently selected from H, substituted or unsubstituted alkyl, substituted or unsubstituted aryl, substituted or unsubstituted aralkyl groups and wherein $R^1$ and $R^2$ can be joined as a substituted or unsubstituted cycloalkyl group and M is selected from H and a cationic center.

A preferred class of compounds of formula I have the structure II below wherein $R^1$ and $R^2$ are alkyl groups.

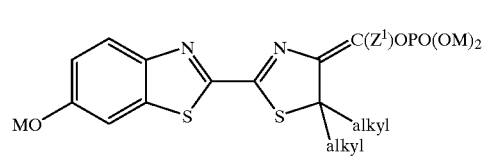

Other preferred compounds of formula I having the structures III and IV shown below, $R^1$ and $R^2$ are alkyl groups, and $Z^1$ is selected from O—Ar and S—Ar groups wherein Ar is a substituted or unsubstituted aryl group.

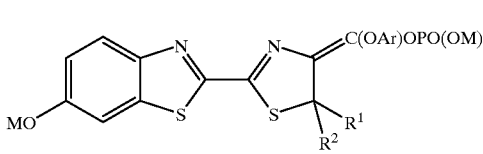

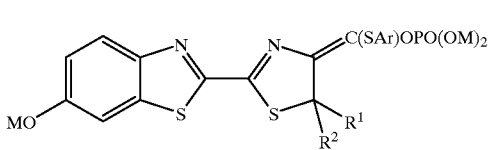

Preferably $R^1$ and $R^2$ are each a lower alkyl group having 1–8 carbon atoms, more preferably from 1–4 carbon atoms and more preferably a methyl group. M is preferably an alkali metal cation and more preferably a lithium, sodium or potassium ion. Preferably the aryl group Ar is a substituted or unsubstituted phenyl or a substituted or unsubstituted naphthyl group.

Compounds in which M is hydrogen or an alkali metal ion are preferred for use in aqueous solutions of neutral to alkaline pH because of their high water solubility. It is recognized that such compounds have ionic groups and as such will ionize in solution and reversibly ion pair with available ions of opposite charge including buffer salts.

When it is stated that red chemiluminescence is produced by reaction of a phosphatase enzyme with a compound of formula I it is meant that either double bond isomer can be used as well as mixtures of the two isomers in any proportion. Double bond isomer as used herein refers to the two geometric isomers formed by interchange of the substituents at one terminus of the exocyclic double bond.

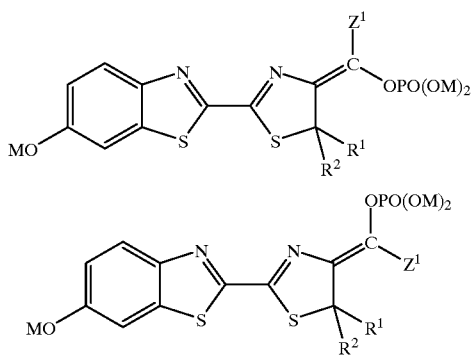

Compounds of any of formulas I–IV are useful for producing red chemiluminescence by reaction with a phosphatase enzyme. Reaction of a compound of formula I with the enzyme produces easily detected red chemiluminescence. Light intensity reaches a maximum level within minutes at room temperature when the reaction is conducted at alkaline pH. The reaction is conducted optionally in the presence of an enhancer.

Light emitted by the present method can be detected by any suitable known means, but is most advantageously detected by a CCD or a red sensitive photodiode. Choice of the detection device will be governed by the application and considerations of cost, convenience, and whether creation of a permanent record is required. The red sensitivity of CCD-based detectors takes best advantage of the red chemiluminescence produced in accordance with the present methods. The combination of CCD imaging and enzymatic generation of red chemiluminescence provides an unexpectedly powerful tool for detection of nucleic acid and protein analytes when using blotting techniques such as Southern, northern and western blotting. Detection sensitivity, signal strength and duration can exceed the performance of other chemiluminescent phosphatase substrates in commercial use when visualized with a CCD camera imaging system.

In a method according to the invention, compound I is reacted with a phosphatase enzyme to produce the chemiluminescence. In a preferred method, the compound of formula I has a phosphate salt group and the reaction is conducted in an alkaline buffer with a pH between about 8 and 10 to produce red chemiluminescence. Analytical sensitivity can be increased by incorporation of various ancillary reagents as will be described in more detail below. Enzymatic reactions are performed at a temperature between 5° C. and 50° C., preferably between 20° C. and 40° C. in an aqueous buffer solution at a pH between 7 and 10.5, preferably between 8.5 and 10. Compound I is used at a concentration between 1 $\mu$M and 20 mM, preferably between 10 $\mu$M and 1 mM.

Phosphatase enzymes useful in the present chemiluminescent reactions include alkaline phosphatase from a bacterial source such as *E. coli*, mammalian alkaline phosphatase, acid phosphatase from plant or mammalian sources and conjugates of such enzymes.

Incorporation of certain cationic aromatic compounds into a reaction mixture comprising a phosphatase enzyme and the chemiluminescent substrate greatly increases the amount of chemiluminescence. A listing of effective cationic aromatic compounds is provided in Applicant's published PCT application WO97/26245. Preferred compounds include lucigenin, Basic Blue 41, Basic Blue 66 and Methylene Blue. Nonionic surfactants can be used in addition as additives in the present chemiluminescent reactions to improve analytical sensitivity. Nonionic surfactants useful in the practice of the present invention include, by way of example, polyoxyethylenated alkylphenols, polyoxyethylenated alcohols, polyoxyethylenated ethers, polyoxyethylenated sorbitol esters, and polyoxyethylene-polyoxypropylene copolymers.

Cationic surfactants such as quaternary ammonium and phosphonium salt compounds, including polymeric compounds as disclosed in U.S. Pat. No. 5,393,469, can be used in conjunction with the present chemiluminescent reactions. Examples include poly(vinylbenzyltrialkylphosphonium) polymers such as poly(vinylbenzyltributylphosphonium) polymer.

The reactions of the present invention are conveniently carried out in solution such as an aqueous buffer which may be in contact with the surface of a solid support such as a bead, tube, membrane or microwell plate coated with enzyme. Suitable buffers include any of the commonly used buffers capable of maintaining a pH in the range of about 6 to about 10 for example, phosphate, borate, carbonate, tris(hydroxymethylamino)methane, glycine, glucamine, tricine, 2-amino-2-methyl-1-propanol ("221"), diethanolamine and the like. Buffer solutions can contain mixtures of more than one buffering compound. The preferred method of practicing the invention in this regard is determined by the requirements of the particular intended use.

Since the reaction is catalyzed by the phosphatase enzyme, exceedingly small quantities of the enzyme are sufficient to produce a detectable amount of light. Sensitivities of 0.01 attomol ($1\times10^{-20}$ mol) have been achieved. The ability to detect such small amounts of enzymes make the present chemiluminescent technology suitable for high-sensitivity analyses of many types of analytes using enzyme-linked assays.

An important use of the present chemiluminescent methods is for detecting the presence or amount of an analyte in an assay procedure by a chemiluminescent reaction. The method comprises the steps of contacting a sample suspected of containing the analyte with a chemiluminescent compound of the present invention and, if not present in the sample, a phosphatase enzyme, detecting the light produced in a qualitative method and, if quantitation is desired, relating the amount of light produced to the amount of the analyte. The relationship between light intensity and amount of analyte can be easily discerned by constructing a calibration curve with known amounts of the analyte. The chemiluminescent compound is typically used in a concentration of about $10^5$ M to about $10^{-2}$ M, preferably between about $10^{-4}$ M and about $10^{-3}$ M. The enzyme is preferably below about $10^{-9}$ M when detected in a solution. Typical samples which are analyzed by the chemiluminescent reaction method are body fluids such as blood, plasma, serum, urine, semen, saliva, CSF and the like as well as food and environmental samples.

Analytes which can be assayed by the present methods include phosphatase enzymes, in which case it would be unnecessary to add additional enzyme, phosphatase inhibitors, and various classes of organic and biological molecules which can be directly or indirectly labeled with a phosphatase enzyme. Techniques and formats for performing enzyme-labeled assays and enzyme-labeled specific binding assays are widely known in the art. Some examples for purposes of illustrating ways of performing assays in accordance with the present invention are presented below.

In a first exemplary method, the phosphatase enzyme is directly attached to an analyte as a label. In a second exemplary method, the enzyme is attached to a compound with a specific binding affinity for the analyte. An example of this embodiment is an enzyme-labeled antibody to the analyte. In a third exemplary method, an analyte binding compound is bound to at least one enzyme-labeled specific binding substance for the analyte binding compound. Examples of this embodiment include an unlabeled primary antibody to the analyte being bound to an enzyme-labeled secondary antibody or an unlabeled first oligonucleotide which is complementary to a nucleic acid analyte, and hybridization of the first oligonucleotide to one or more labeled oligonucleotides. In a fourth exemplary method, an analyte binding compound can be labeled with at least one second specific binding substance which is then bound to an enzyme-labeled binding partner for the second specific binding substance. An example of the fourth method an avidin-labeled anti-analyte antibody is reacted with biotin-enzyme conjugates.

As mentioned above, the analyte can be the phosphatase enzyme used to catalyze the chemiluminescent reaction. Such an assay method is useful e.g. in detecting enzyme levels in clinical specimens due to the speed and sensitivity afforded by use of the present chemiluminescent reactions. Techniques for performing enzyme assays are well known. With the guidance provided by the examples as taught herein, variations of procedures for preparing samples, determining appropriate quantities and ratios of reagents, reaction times, constructing calibration curves and the like will be within the ability of one of ordinary skill in the art to devise as a matter of routine experimentation.

The analyte can be an enzyme inhibitor in another embodiment. A method for detecting an enzyme inhibitor in a sample comprises contacting the sample with the appropriate enzyme and a compound of formula I and detecting a property of the chemiluminescence. Measurement of the quantity or characteristics of an inhibitor, such as the inhibition constant $K_i$, or half-life for inhibition, $t_{1/2}$, are made by measuring light produced by action of the enzyme on a compound of formula I in the presence of the inhibitor and in the absence of the inhibitor and the results are compared. The presence of the inhibitor can be measured by its effect of a decrease in light intensity, a slower rate of rise of light intensity or a delay period before light emission begins. Inhibitors of phosphatase include inorganic phosphate and levamisole.

In another type of assay, a phosphatase enzyme is conjugated to one member of a specific binding pair. An example is a chemiluminescent enzyme-linked immunoassay, such as the so-called enzyme-linked immunosorbent assay or ELISA. Such assays are commonly used in manual format as well as on automated multi-test immunoassay systems. In a typical immunoassay, the analyte hapten, antigen or antibody is assayed by detecting the presence or amount of an enzyme-labeled specific binding partner for the analyte or an enzyme-labeled analog of the analyte. Various assay formats and the protocols for performing the immunochemical steps are well known in the art. These assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies, one of which is detectably labeled, with the analyte. The detectably labeled binding pair so formed can be assayed with the compounds and methods of the present invention. When the detectable label is the enzyme, it is detected directly. When the detectable label is a member of another specific binding pair, e.g. a hapten, a conjugate of its binding partner with an enzyme is reacted first and the enzyme then detected in accordance with the present methods. Measurement can be performed with enzyme-labeled species attached to a solid surface or support including beads, tubes, microwells, magnetic particles, test strips, membranes and filters such as are in common use in the art. The detectable enzyme-labeled species can also be present free in solution or enclosed within an organized assembly such as a liposome in which case a lytic agent is employed to lyse the liposome and free the detectable enzyme.

Another exemplary use is the detection of proteins by the technique of Western blotting. A sample containing a protein analyte is separated electrophoretically. The separated proteins are blotted onto a membrane and probed with a specific primary antibody and an enzyme-labeled secondary antibody with affinity for the primary antibody. The marker enzyme is detected by catalysis of the chemiluminescent reaction; the occurrence of chemiluminescence reflects the presence of the analyte protein. Variations on this technique such as using enzyme-labeled primary antibodies, biotinylated antibodies and avidin-AP and the like are considered within the scope of assays able to be performed using the inventive methods.

Another area of application of the present detection methods is the detection of nucleic acids by the use of enzyme-labeled nucleic acid probes. Methods for analysis and chemiluminescent detection of nucleic acids using enzyme labels are well established techniques and include solution hybridization assays, DNA detection in Southern blotting, RNA by Northern blotting, DNA sequencing, DNA fingerprinting, colony hybridizations and plaque lifts. The enzyme label can be present as a direct conjugate with a probe oligonucleotide or capture oligonucleotide or it can be incorporated through indirect linking means using art-known methods. Examples of indirect linking means include using hapten-labeled oligonucleotides and antihapten-enzyme conjugates or biotinylated oligonucleotides and avidin-enzyme conjugates. Such nucleic acid assays can be performed on a blotting membrane or in solution using oligonucleotides attached to solid surfaces including beads, tubes, microwells, magnetic particles or test strips such as are known in the art.

Other specific binding pairs useful in assay methods performed in accord with the present invention include complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

In another aspect, the present invention relates to reagent compositions for producing chemiluminescence by reaction with an enzyme. A preferred reagent composition or producing chemiluminescence by reaction with a phosphatase comprises an aqueous buffer having a pH in the range of about 8 to 10, a compound of formula I containing phosphate salt group as one of the groups $Z^1$ or $Z^2$, at a concentration of 0.001–10 mM, preferably in the range 0.01–1 mM and a cationic aromatic compound at a concentration of 0.001–10 mM, preferably in the range 0.01–1 mM.

Another aspect of the invention is to provide compounds of formula V which are useful as synthetic intermediates in preparing compounds of formulas I.

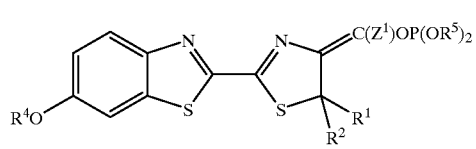

V

In compounds of formula V, $Z^1$ is a group selected from $OR^3$ and $SR^3$ and $R^3$ is selected from substituted or unsubstituted alkyl, substituted or unsubstituted aryl, and substituted or unsubstituted aralkyl groups, $R^1$ and $R^2$ are independently selected from H, substituted or unsubstituted alkyl, substituted or unsubstituted aryl, substituted or unsubstituted aralkyl groups and wherein $R^1$ and $R^2$ can be joined as a substituted or unsubstituted cycloalkyl group, $R^4$ is a protecting group selected from a trialkylsilyl group, an alkyldiarylsilyl group, an alkylcarbonyl (e.g. acetyl and pivaloyl) and an arylcarbonyl (e.g. benzoyl) group, one $R^5$ group is a protecting group selected from substituted alkyl, trialkylsilyl, alkyldiarylsilyl and aralkyl groups, the other $R^5$ group is selected from substituted alkyl, trialkylsilyl, alkyldiarylsilyl and aralkyl groups or an alkali metal ion. Exemplary substituted alkyl groups which can serve as the $R^5$ group include 2-cyanoethyl and 2-trimethylsilylethyl groups.

In order to more fully describe various aspects of the present invention, the following examples are presented which do not limit the scope of the invention in any way.

EXAMPLES

Example 1 Synthesis

The following compounds are prepared as described below.

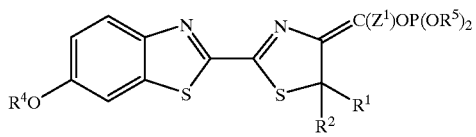

| Compound | $Z^1$ | $R^1$ & $R^2$ | M |
|---|---|---|---|
| 1 | Ph-O | H | Na |
| 2 | Ph-S | H | Na |
| 3 | 4-ClC$_6$H$_4$-S | H | Na |
| 4 | Ph-S | CH$_3$ | Na |
| 5 | 4-ClC$_6$H$_4$-S | CH$_3$ | Na |
| 6 | Np-S | CH$_3$ | Na |

-continued

| Compound | $Z^1$ | $R^1$ & $R^2$ | $R^4$ | $R^5$ |
|---|---|---|---|---|
| 7 | Ph-O | H | Piv | CH$_2$CH$_2$CN |
| 8 | Ph-S | H | Piv | CH$_2$CH$_2$CN |
| 9 | 4-ClC$_6$H$_4$-S | H | Piv | CH$_2$CH$_2$CN |
| 10 | Ph-S | CH$_3$ | Piv | CH$_2$CH$_2$CN |
| 11 | 4-ClC$_6$H$_4$-S | CH$_3$ | Piv | CH$_2$CH$_2$CN |
| 12 | Np-S | CH$_3$ | Piv | CH$_2$CH$_2$CN |
| 13 | Ph-S | CH$_3$ | TBDPS | CH$_2$CH$_2$CN |

Ph = phenyl, 4-ClC$_6$H$_4$-S = p-chlorophenylthio, Np = 2-naphthyl, Piv = pivaloyl (trimethylacetyl), TBDPS = t-butyldiphenylsilyl In the synthesis of compounds 1–13, two isomers can be produced. When two isomers were separated they are designated isomer 1 and isomer 2 on the basis of their order of elution during silica gel chromatography. Tentative stereochemical assignments are described in Example 20.

Example 2 Synthesis of Compounds 5 and 11

2-Cyano-6-pivaloyloxybenzothiazole. A solution of 2-cyano-6-hydroxybenzothiazole (2.1 g, 12.5 mmol) in 30 mL of dry THF under inert atmosphere was treated with pyridine (2.0 g, 25 mmol) followed by pivaloyl chloride (1.95 g, 16.2 mmol). This reaction was stirred 15 h at room temperature. The reaction mixture was then diluted with 100 mL of distilled water, and this solution was extracted with ethyl acetate (4×50 mL). The combined organics were washed with aqueous sodium bicarbonate (2×100 mL) and distilled water (1×100 mL), then dried over Na$_2$SO$_4$ and concentrated under reduced pressure to afford 3.0 g of a thick oil. This material was chromatographed on silica gel and 1.8 g of the product was eluted with 10% ethyl acetate/hexanes. $^1$H NMR (CDCl$_3$): δ 1.39 (s, 9H); 7.34–7.38 (m, 1H); 7.74–7.75 (d, 1H) ; 8.20–8.23 (d, 1H).

2-(6-Pivaloyloxy-2-benzothiazolyl)-5,5-dimethyl-Δ$^2$-thiazoline-4-carboxylic acid. 2-Cyano-6-pivaloyloxybenzothiazole (1.25 g, 4.8 mmol) was dissolved in MeOH (30 mL, oxygen-free) and the solution was bubbled with argon. DL-Penicillamine (0.789 g, 5 mmol) in 15 mL of water and 50 mg of sodium carbonate (pH 8) was also bubbled with argon for 5–10 min and then added dropwise to the MeOH solution. During the addition a white precipitate formed in the reaction mixture, which redissolved with the addition of another 5 mL of MeOH. The light yellow solution was bubbled with argon at room temperature over 45 min. The reaction volume was concentrated by a half, and acidified with 1:1 concentrated HCl:Type I water (2 mL). A white precipitate formed, which was taken up in ethyl acetate. The organic layer washed with water, dried over Na$_2$SO$_4$ and concentrated to afford 1.86 g of an white solid. $^1$H NMR (CD$_3$COCD$_3$): δ 1.37 (s, 9H); 1.55 (s, 3H); 1.82 (s, 3H); 5.01 (s, 1H); 7.34–7.37 (dd, 1H); 7.92 (d, 1H); 8.09–8.13 (d, 1H).

p-Chlorophenyl 2-(6-pivaloyloxy-2-benzothiazolyl)-5,5-dimethyl-Δ$^2$-thiazoline-4-thiocarboxylate. DCC (0.684 g, 3.3 mmol) was added to a solution of 2-(6-pivaloyloxy-2-benzothiazolyl)-5,5-dimethyl-Δ$^2$-thiazoline-4-thiocarboxylate (1.0 g, 2.55 mmol) in 30 mL of dry THF to give a dark red solution. After 2–3 min, p-chlorothiophenol (0.553 g, 3.8 mmol) was added, forming a pale yellow solution which was stirred for 2 h. The reaction was allowed to stand at −20° C. for 1 h and the resultant white precipitate was filtered off. The filtrate was concentrated to dryness and the crude product was chromatographed over silica gel, eluting with 30% CH$_2$Cl$_2$/hexanes to afford 360 mg of product. $^1$H NMR (CD$_3$COCD$_3$) δ 1.37 (s, 9H) ; 1.54 (s, 3H) ; 1.83 (s, 3H); 5.15 (s, 1H); 7.37–7.55 (m, 5H); 7.96–7.97 (d, 1H); 8.14–8.17 (d, 1H).

Compound 11. Diisopropylamine, 0.136 mL (0.97 mmol) and 10 mL of anhydrous THF were added via syringe to a 100 mL three-necked round bottom flask equipped with an addition funnel under inert atmosphere. The solution was cooled to −78° C., at which point n-butyllithium (0.39 mL, 0.97 mmol) was added via syringe and the reaction was stirred for 15 min. A solution of the thioester from the previous step (0.36 g, 0.69 mmol) in 12 mL of THF was added to the reaction mixture over 10 min and the resultant dark red solution was stirred at −78° C. for 1 h. A solution of 0.5 mL of dry THF, pyridine (0.8 mL) and POCl$_3$ (0.113 mL, 1 mmol) was added dropwise to the cold solution and the mixture stirred 30 min at −78° C. The reaction mixture was allowed to warm to room temperature. After stirring 1 h at room temperature, 2-hydroxypropionitrile (0.331 mL, 4.8 mmol) was added and the reaction stirred for 2.5 h. The solution was stored over night at −20° C. The precipitate was collected by filtration, washed with THF and discarded. The filtrate was concentrated and the resultant material was taken up in ethyl acetate and washed with water. The organic layer was dried and concentrated and the crude product was chromatographed on a column of silica gel. Isomer 1 was eluted with 50% ethyl acetate/hexanes and yielded 65.3 mg; isomer 2 was eluted with 70% ethyl acetate/hexanes and yielded 51 mg.

Isomer 1: $^1$H NMR (CDCl$_3$): δ 1.39 (s, 9H); 1.99 (s, 6H); 2.74–2.78 (t, 4H); 4.30–4.36 (m, 4H); 7.25–8.14 (m, 7H). $^{31}$P NMR (CDCl$_3$): δ −9.82 to −9.55.

Isomer 2: $^1$H NMR (CDCl$_3$): δ 1.39 (s, 9H); 1.95 (s, 6H); 2.74–2.78 (m, 4H); 4.26–4.47 (m, 4H); 7.215–8.10 (m, 7H). $^{31}$P NMR (CDCl$_3$): δ −9.44 to −9.17.

Compound 5 (Isomer 1). A 65.3 mg portion of compound 11, isomer 1 (93 μmol) in 6 mL of acetone was cooled to 0° C. in an ice bath and bubbled with argon. To this solution was added 296 μL of 1N aqueous sodium hydroxide (0.29 mmol) and 296 μL of water. Reaction mixture color became dark red upon addition of the base and gradually became orange during 1 hour of stirring. After 1 h, a precipitate formed in the solution. The reaction mixture was allowed to stir at room temperature 18 h. Then the reaction mixture was centrifuged, washed with acetone, centrifuged again, and dried to afford 49 mg of an orange solid (96%). $^1$H NMR (D$_2$O): δ 1.86 (s, 6H) ; 6.85–6.89 (dd, 1H) ; 7.06–7.07(d, 1H); 7.34 (s, 4H); 7.72–7.75 (d, 1H). $^{31}$P NMR (D$_2$O) 0.404.

Compound 5 (Isomer 2). A 51 mg portion of compound 11, isomer 2 (92 μmol) in 5 mL of acetone was reacted with 232 μL of 1N aqueous sodium hydroxide (0.23 mmol) and 250 μL of water in the same manner to afford 34 mg of orange solid (81%). $^1$H NMR (D$_2$O): δ 1.89 (s, 6H); 6.82–6.86 (dd, 1H); 7.00 (d, 1H); 7.26–7.45 (dd, 4H); 7.64–7.67 (d, 1H). $^{31}$P NMR (D$_2$O): 0.107.

Example 3 Synthesis of Compounds 2 and 8

2-(6-Pivaloyloxy-2-benzothiazolyl)-Δ$^2$-thiazoline-4-carboxylic acid. 2-Cyano-6-pivaloyloxybenzothiazole (1.35 g, 5 mmol) was dissolved in 30 mL of MeOH and the solution was bubbled with argon. Cysteine (0.692 g, 5.7 mmol) was dissolved in 7 mL of water and the pH of the solution was adjusted to 8 with sodium carbonate. The aqueous solution was saturated with argon and added dropwise to the MeOH solution. The resultant light yellow solution was bubbled with argon at room temperature for 30 min. The reaction was cooled to 0° C. and acidified with 1:1 concentrated HCl:Type I water (1 mL). The solution was diluted with ethyl acetate, concentrated to 20 mL volume and extracted with ethyl acetate (3×50 mL). The combined organics were washed with water, dried over Na$_2$SO$_4$ and concentrated to afford 1.96 g of a white solid. $^1$H NMR (CD$_3$COCD$_3$): δ 1.37 (s, 9H); 3.82–3.86 (dd, 2H); 5.49 (t, 1H); 7.35–7.38 (dd, 1H); 7.92–7.93 (d, 1H); 8.11–8.14 (d, 1H).

Phenyl 2-(6-pivaloyloxy-2-benzothiazolyl)-Δ$^2$-thiazoline-4-thiocarboxylate. DCC (0.736 g, 3.5 mmol) was added to a solution of the previous carboxylic acid (1.0 g, 2.7 mmol) in 20 mL of dry THF to give a dark red solution. Thiophenol (0.423 mL, 4 mmol) was added, forming a pale yellow solution which stirred for 2 h. The white urea by-product was collected by filtration, washed with THF and discarded. The filtrate was concentrated to a volume of 10 mL under reduced pressure. The crude product was diluted with 4 mL of hexane and stored at −20° C. for 18 h. Additional urea by-product was removed and the filtrate was washed with hexanes several times. The combined hexane washes were concentrated and the product was chromatographed over silica gel, eluting with 30% CH$_2$Cl$_2$/hexanes, followed by 20% ethyl acetate in hexanes to afford 124 mg of product. The remaining filtrate layer was also chromatographed over silica gel in the same manner and the products pooled (660 mg). $^1$H NMR (CD$_3$COCD$_3$): δ 1.38 (s, 9H); 3.82–3.97 (m, 2H); 5.77–5.83 (m, 1H); 7.38–7.46 (m, 6H); 7.97–7.98 (d, 1H); 8.15–8.18 (d, 1H).

Compound 8. A solution of diisopropylamine (132 μL, 0.94 mmol) in 5 mL of dry THF under inert atmosphere was cooled to −78° C. and n-butyllithium (376 μL, 0.94 mmol) was added via syringe. After the reaction cooled 15 min, a solution of the thioester (330 mg, 0.72 mmol) in 10 mL of THF was added to the reaction mixture dropwise. The resultant dark red solution was stirred at −78° C. for 50 min. A solution of pyridine (0.58 mL, 7.2 mol) and POCL$_3$ (118 μL, 1.2 mmol) in 2 mL of dry THF was added to the cold solution dropwise and the mixture stirred 45 additional min at −78° C. The cold bath was removed and the reaction mixture was allowed to warm to room temperature, during which time the reaction mixture changed from dark red to orange. The reaction was cooled briefly in an ice bath and 2-hydroxypropionitrile (360 mg, 5 mmol) was injected into the reaction, followed by 300 μL of pyridine. The reaction stirred at room temperature for 18 h. The precipitate was collected by filtration, washed with THF and discarded. The filtrate was concentrated under reduced pressure and the residue was taken up in ethyl acetate and washed with water (2×50 mL). The organic layer was dried and concentrated and the crude product was loaded on a column of silica gel. Two isomers were eluted from the column in 75–80% ethyl acetate in hexanes. Isomers 1 and 2 were separately purified by prep. TLC, Isomer 1 was eluted with 60% ethyl acetate/hexanes to obtain 5 mg. Isomer 2 was eluted with 75% ethyl acetate/hexanes to obtain 9 mg.

Isomer 1: $^1$H NMR (CDCl$_3$): δ 1.39 (s, 9H) ; 2.77 (t, 4H) 4.33–4.45 (m, 6H); 7.26–7.48 (m, 6H); 7.69–7.70 (d, 1H); 8.13–8.16 (d, 1H). $^{31}$P NMR (CDCl$_3$): −9.67–(−9.39).

Isomer 2: $^1$H NMR (CDCl$_3$): δ 1.39 (s, 9H) ; 2.67–2.76 (m, 4H); 4.20–4.30 (m, 4H); 4.55–4.57 (d, 2H); 7.32–7.49 (m, 6H); 7.66–7.67 (d, 1H); 8.11–8.15 (d, 1H). $^{31}$P NMR (CDCl$_3$) −9.56–(−9.32).

Compound 2 (Isomer 1). 4.5 mg of compound 8, isomer 1 (7.0 μmol) in 5 mL of acetone was cooled to 0° C. in an ice bath and bubbled with argon. To this solution was added 112 µL of 0.2 N aqueous sodium hydroxide (22 µmol) and 112 µL of water. The reaction mixture color became dark red upon addition of the base and gradually became orange with stirring. The reaction mixture was allowed to stir at room temperature 18 h under argon. Precipitate was observed in the reaction mixture so the solvent was decanted and the remaining solid material was washed with acetone, centrifuged and dried to afford 2.5 mg of solid. $^1$H NMR (D$_2$O): δ 4.25 (d, 2H); 6.85–7.75 (m, 8H).

Compound 2 (Isomer 2). Compound 8, isomer 2 (9 mg, 14 µmol) in 5 mL of acetone was reacted with 224 µL of 0.2 N aqueous sodium hydroxide (45 µmol) and 225 µL of water in the same manner to afford 6.4 mg of solid. $^1$H NMR (D$_2$O): δ 4.50–4.52 (d, 2H); 6.82–7.72 (m, 8H).

Example 4 Synthesis of Compounds 4 and 13

2-Cyano-6-t-butyldiphenylsiloxy-benzothiazole. A solution of 2-cyano-6-hydroxybenzothiazole (5.0 g, 28 mmol) in 100 ml of anhydrous DMF under inert atmosphere was treated with 2.9 g of imidazole (4.2 mmol) followed by t-butyldiphenylchlorosilane (9.34 g, 34 mmol). The reaction was stirred at room temperature for 3 h and then diluted with 200 ml of ethyl acetate and washed with water (4×400 ml). The organic layer was dried over sodium sulfate and concentrated under reduced pressure. The crude product was purified by column chromatography, eluting with 5–10% ethyl acetate/hexanes to afford 13.0 g of the desired product containing ~10% silyl impurity in quantitative yield. The product was taken on without further purification. $^1$H NMR (CDCl$_3$): δ 1.12 (s, 9H); 7.13–7.46 (m, 8H); 7.70–7.72 (m, 4H); 7.92–7.95 (d, 1H).

2-(6-t-Butyldiphenylsiloxy-2-benzothiazolyl)-5,5-dimethyl-Δ$^2$-thiazoline-4-carboxylic acid. 2-Cyano-6-t-butyldiphenylsiloxybenzothiazole (13.0 g, 31 mmol) was dissolved in MeOH (500 mL, oxygen-free) in a three-necked round bottom flask and the solution was bubbled with argon. DL-penicillamine (4.9 g, 33 mmol) was dissolved in 90 mL of water and pH of the solution was adjusted to 8 with sodium carbonate. The aqueous solution was saturated with argon and added dropwise to the MeOH solution. The reaction was bubbled with argon at room temperature for 1.5 h. A sticky precipitate formed during the reaction, which redissolved with the addition of 15 mL of MeOH. The reaction was concentrated to remove most of the MeOH and the remaining aqueous solution was acidified with 1:1 concentrated HCl:Type I water (6 mL). The resultant white precipitate was extracted into 350 mL of ethyl acetate. The organic layer was washed with water (4×200 mL), dried over sodium sulfate and concentrated to afford 16.0 g of the product containing 10% silyl impurity (94%). The product was taken on without further purification.

Phenyl 2-(6-t-butyldiphenylsiloxy-2-benzothiazolyl)-5,5-dimethyl-Δ$^2$-thiazoline-4-thiocarboxylate. DCC (0.635 g, 3 mmol) was added to a solution of the previous carboxylic acid (1.3 g, 2.4 mmol) in 30 mL of dry THF. Thiophenol (0.468 g, 4.3 mmol) was added and the reaction stirred for 2 h. The white urea by-product was collected by filtration and discarded. The filtrate was concentrated to a thick liquid under reduced pressure, which was chromatographed over silica gel, eluting with 5% ethyl acetate/hexanes to remove excess thiophenol, followed by 10–15% ethyl acetate/hexanes to afford 0.38 g of product (24%). $^1$H NMR (CDCl$_3$): δ 1.13 (s, 9H); 1.53 (s, 3H); 1.79 (s, 3H); 4.87 (s, 1H); 6.99–7.04 (m, 1H); 7.22–7.23 (d, 1H); 7.32–7.43 (m, 11H); 7.70–7.74 (m, 4H); 7.85–7.88 (d, 1H).

Alternate Preparation of the Thioester Carbonyldiimidazole (1.92 g, 12 mmol) was added to a solution of the carboxylic acid (5.0 g, 9.1 mmol) in 50 mL of dry CH$_3$CN under inert atmosphere. After stirring for 2 min, thiophenol (1.2 g, 0.01 mol) was added and the reaction stirred for 1 h. The solvent was removed under reduced pressure and the crude solid was chromatographed over silica gel, eluting with 5% ethyl acetate/hexanes to remove excess thiophenol, followed by 12% ethyl acetate/hexanes to afford 1.9 g of product (32%).

Compound 13. Diisopropylamine 0.73 mL (5 mmol) was added via syringe to 50 mL of dry THF under argon. The solution was cooled to −78° C. and n-butyllithium (2.02 mL, 5 mmol) was added via syringe. After the reaction cooled for 20 min, a solution of the preceding thioester (2.5 g, 3.9 mmol) in 50 mL of dry THF was added via dropping funnel to the reaction mixture. The solution was stirred at −78° C. for 1 h. Pyridine (3.0 g, 38 mmol) and POCl$_3$ (0.6 mL, 6.2 mmol) were added to the dropping funnel and the mixture was added to the cold solution dropwise. The mixture stirred 15 min at −78° C., at which time the cold bath was removed and the reaction mixture warmed to room temperature and stirred for 1 hour. Hydroxypropionitrile (2.8 g, 39 mmol) was injected into the reaction and the reaction stirred for 4 h at room temperature and stored for 15 h at 4° C. The reaction mixture was concentrated under reduced pressure and the remaining material was taken up in 100 mL of ethyl acetate and washed with water. The organic layer was dried and concentrated under reduced pressure and the crude product (3 g) was purified by column chromatography, eluting with 10–85% ethyl acetate/hexanes to yield 0.38 g of isomer 1 and 0.92 g of isomer 2.

Isomer 1: $^1$H NMR (CDCl$_3$): δ 1.12 (s, 9H); 1.98 (s, 6H) 2.65–2.69 (t,4H); 4.19–4.38 (m, 4H); 6.98–7.02 (m, 1H); 7.24–7.43 (m, 12H); 7.71–7.74 (m, 4H); 7.83–7.86 (d, 1H). $^{31}$P NMR (CDCl$_3$): −10.13 to (−9.85).

Isomer 2: $^1$H NMR (CDCl$_3$): δ 1.12 (s, 9H); 1.95 (s, 6H) 2.64–2.69 (m, 4H); 4.19–4.35 (m, 4H); 6.97–7.00 (m, 1H); 7.15–7.43 (m, 12H); 7.69–7.72 (m, 4H); 7.80–7.83 (d, 1H). $^{31}$P NMR (CDCl$_3$): −9.71 to (−9.45).

Compound 4 (Isomer 1). Compound 13, isomer 1 (0.15 g, 0.18 mmol) in 8 mL of acetone was bubbled with argon. To this solution was added 800 µL of 0.675 N aqueous sodium hydroxide (0.54 mmol). The reaction mixture was allowed to stir at room temperature for 18 h under argon. Precipitate was observed in the reaction mixture so the solvent was decanted and the remaining solid material was triturated with 5 mL of acetone. The solid was collected by filtration, washed with additional acetone and dried to afford 100 mg of solid. $^1$H NMR (D$_2$O): δ 1.88 (s, 6H); 6.85–6.89 (m, 1H); 7.06–7.07 (d, 1H); 7.22–7.24 (t, 1H); 7.33–7.38 (m, 4H); 7.72–7.75 (d, 1H). $^{31}$P NMR (D$_2$O): 0.38

Compound 4 (Isomer 2). Compound 13, isomer 2 (0.21 g, 0.26 mmol) in 8 mL of acetone was reacted with 1.0 mL of 0.75 N aqueous sodium hydroxide (0.76 mmol) in the same manner to afford 120 mg of product. $^1$H NMR (D$_2$O): δ 1.90 (s, 6H); 6.80–6.83 (d, 1H); 6.97 (s,1H); 7.14–7.17 (t, 1H); 7.26–7.31 (t, 2H); 7.46–7.48 (d, 2H); 7.63–7.66 (d, 1H). $^{31}$P NMR (D$_2$O): 0.07.

Example 5 Synthesis of Compounds 6 and 12

Carbonyldiimidazole (0.537 g, 3.3 mmol) was added to a solution of 2-(6-pivaloyloxy-2-benzothiazolyl)-5,5-dimethyl-Δ$^2$-thiazoline-4-carboxylic acid (1.0 g, 2.6 mmol) in 30 mL of CH$_3$CN to give a dark red solution. Thionaphthol (0.654 g, 4 mmol) was added, forming a light orange solution. The solution became thick with precipitate, so another 30 mL of CH$_3$CN was added to the reaction. After 20 min, the reaction mixture was filtered to afford 0.8 g of white powder, which proved to be pure product by $^1$H NMR. The filtrate was concentrated and chromatographed over silica gel, eluting with 15% ethyl acetate/hexanes to afford an additional 0.53 g of thioester (total 1.33 g, 98%). $^1$H NMR (CD$_3$COCD$_3$): δ 1.38 (s, 9H); 1.59 (s, 3H); 1.84 (s, 3H); 5.18 (s, 1H); 7.38–7.62 (m, 4H); 7.97–8.18 (m, 6H).

Compound 12. Diisopropylamine 169 μL (1.2 mmol) was added via syringe to 10 mL of dry THF under inert atmosphere. The solution was cooled to −78° C., and n-butyllithium (482 μL, 1.2×10–3 mol) was added via syringe. After the reaction cooled for 15 min, a solution of the thioester (460 mg, 0.86 mmol) in 14 mL of THF was added to the reaction mixture dropwise via syringe. The dark red solution was stirred at −78° C. for 1 h. A solution of pyridine (1.0 mL, 12.9 mmol) and POCl$_3$ (140 μL, 1.46 mmol) in 0.7 mL of dry THF was added dropwise via syringe and the mixture stirred for 35 min at −78° C. The reaction mixture was allowed to warm to room temperature for 1 h, during which time the reaction mixture changed from dark red to yellow. The reaction was cooled briefly in an ice bath and 2-hydroxypropionitrile (550 μL, 8 mmol) was injected into the reaction which was stirred on ice for 20 min and then over night at room temperature. The precipitate was collected by filtration, washed with THF and discarded. The filtrate was concentrated and the resultant material was taken up in ethyl acetate and washed with water (3×30 mL). The organic layer was dried and concentrated and the crude product was chromatographed on a column of silica gel. Isomer 1 (106 mg) was eluted with 50% ethyl acetate/hexanes. Isomer 2 (100 mg) was eluted with 70% ethyl acetate/hexanes and then further purified by prep. TLC.

Isomer 1: $^1$H NMR (CD$_3$COCD$_3$): δ 1.37 (s, 9H) ; 2.07 (s, 6H); 2.86–2.90 (t, 4H); 4.28–4.48 (m, 4H); 7.37–8.17 (m, 10H). $^{31}$P NMR (CD$_3$COCD$_3$): −3.87–(−3.61)

Isomer 2: $^1$H NMR (CD$_3$COCD$_3$): δ 1.36 (s, 9H) ; 2.07 (s, 6H); 2.89–2.94 (t, 4H); 4.37–4.48 (m, 4H); 7.32–8.10 (m, 10H). $^{31}$P NMR (CD$_3$COCD$_3$): −3.87–(−3.62)

Compound 6 (Isomer 1). Compound 12, isomer 1 (105 mg, 0.14 mmol) in 6 mL of acetone was bubbled with argon. To this solution was added 228 μL of 2N aqueous sodium hydroxide (0.45 mmol) and 250 μL of water. Reaction mixture color became dark red upon addition of the base. The reaction mixture was allowed to stir at room temperature 16 h under argon. Precipitate was observed in the reaction mixture so the solvent was decanted and the remaining solid material was washed with acetone (2×1.5 mL), centrifuged and dried to afford 86 mg of solid. $^1$H NMR (D$_2$O): δ 1.87 (s, 6H) ; 6.85–7.87 (m, 10H). $^{31}$P NMR (D$_2$O): 0.425

Compound 6 (Isomer 2). Compound 12, isomer 2 (96 mg, 0.13 mmol) in 6 mL of acetone was reacted with 213 μL of 2N aqueous NaOH (0.43 mmol) in 250 μL of water in the same manner as isomer 1 to afford 70 mg of compound 6, isomer 2. $^1$H NMR (D$_2$O): δ 1.91 (s, 6H); 6.75–6.82 (m, 2H); 7.32–7.84 (m, 7H); 7.96 (s, 1H). $^{31}$P NMR (D$_2$O): 0.156

Example 6 Synthesis of Compounds 1 and 7

DCC (0.736 g, 3.5 mmol) was added to 2-(6-pivaloyloxy-2-benzothiazolyl)-Δ$^2$-thiazoline-4-carboxylic acid (1.0 g, 2.7 mmol) in 30 mL of dry THF to form a dark red solution. Phenol (0.335 mg, 3.5 mmol) was added and the reaction mixture stirred for 1h. The white urea by-product was collected by filtration, washed with THF and discarded. The filtrate was stored at 4° C. over night. Additional urea by-product was removed by filtration. The filtrate was concentrated and chromatographed over a column of silica gel in 30% CH$_2$Cl$_2$/hexanes, eluting with 30–75% CH$_2$Cl$_2$/hexanes and finally neat CH$_2$Cl$_2$ to remove excess phenol, followed by 5% ethyl acetate/CH$_2$Cl$_2$ to afford a mixture of products. This was further purified on a prep. TLC plate, eluting with 20% ethyl acetate/hexanes to give 140 mg. $^1$H NMR (CD$_3$COCD$_3$): δ 1.37 (s, 9H); 3.99–4.02 (d, 2H); 5.79 (t, 1H); 7.22–7.48 (m, 6H); 7.94 (d, 1H); 8.14–8.16 (d, 1H).

Compound 7. A solution of diisopropylamine 65.4 μL (0.46 mmol) in 5 mL of dry THF under Ar was cooled to −78° C. and n-butyllithium (187 μL, 0.46 mmol) was added via syringe. After 15 min, a solution of the phenyl ester (140 mg, 0.33 mmol) in 10 mL of THF was added dropwise via syringe. The dark red solution was stirred at −78° C. for 1 hour. A solution of pyridine (500 μL, 6.1 mmol) and POCl$_3$ (54.2 μL, 0.5.mmol) in 1 mL of dry THF was added dropwise via syringe and the mixture stirred 45 min at −78° C. The reaction mixture was allowed to warm to room temperature for 45 min. The reaction was cooled briefly in an ice bath, 2-hydroxypropionitrile (166 mg, 23 mmol) was injected into the reaction, and the reaction stirred at room temperature for 18 h. The reaction mixture was concentrated under reduced pressure and the residue chromatographed on silica gel with 50% ethyl acetate/hexanes to separate the two isomers. The fraction containing isomer 1 was taken up in ethyl acetate and washed with water, then dried and concentrated. Isomer 1 was purified by prep. TLC, eluting with 60% ethyl acetate/hexanes to give 1 mg. Isomer 2 was obtained in fractions as a mixture with isomer 1

Isomer 1: $^1$H NMR (CDCl$_3$): δ 1.39 (s, 9H) ; 2.75 (m, 4H); 4.25–4.27 (d, 2H); 4.33–4.38 (m, 4H); 7.18–8.15 (m, 8H).

Compound 1. Compound 7 is converted to compound 1 by alkaline hydrolysis of the pivalate and cyanoethyl protecting groups using the procedure of Example 3.

Example 7 Synthesis of Compounds 3 and 9

2-(6-Pivaloyloxy-2-benzothiazolyl)-Δ$^2$-thiazoline-4-carboxylic acid. DL-cysteine (0.84 g, 6.9 mmol) was dissolved in 30 mL of an oxygen-free solution of sodium carbonate at pH 8. Once the cysteine was completely dissolved, the pH was readjusted to 8 by adding sodium carbonate. Argon was bubbled through the solution for 5–10 min, after which time a solution of 2-cyano-6-pivaloyloxybenzothiazole (1.8 g, 6.9 mmol) in MeOH (100 mL, oxygen-free) was added to the solution. The reaction was bubbled with argon at room temperature with occasional shaking over 35–40 min. Then the reaction mixture was acidified with a solution of 0.5 mL concentrated HCl and 0.5 mL water. The solution was quickly extracted with ethyl acetate (3×50 mL) and the combined organics were washed with water, dried over Na$_2$SO$_4$ and concentrated to a thick red liquid which solidified upon standing at 4° C. overnight to afford 2.0 g of an orange-pink solid. $^1$H NMR (CD$_3$COCD$_3$): δ 1.37 (s, 9H); 3.83–3.86 (d, 2H); 5.47–5.53 (t, 1H); 7.35–7.39 (m, 1H); 7.92–7.93 (d, 1H); 8.12–8.15 (d, 1H).

p-Chlorophenyl 2-(6-pivaloyloxy-2-benzothiazolyl)-Δ$^2$-thiazoline-4-thiocarboxylate. DCC (1.44 g, 7 mmol) was added to a solution of 2-(6-pivaloyloxy-2-benzothiazolyl)-Δ$^2$-thiazoline-4-carboxylic acid (2.0 g, 5.4 mmol) in 35 mL of anhydrous THF to give a dark red solution. After 2–3 min, p-chlorothiophenol (1.58 g, 10 mmol) was added, forming a pale yellow solution which was stirred for 2 h. The reaction was allowed to stand at −4° C. for 1 h and the resultant white precipitate (urea by-product) was collected and washed with THF (2×10 mL) and discarded. The filtrate was concentrated to dryness under reduced pressure and the crude solid was washed with hexanes (3×50 mL) to remove any remaining p-chlorothiophenol. The remaining solid was dried under vacuum to afford 1.4 g of clean product. $^1$H NMR (CDCl$_3$): δ 1.39 (s, 9H); 3.79–3.84 (m, 2H); 5.55–5.60 (m, 1H); 7.25–7.28 (m, 1H); 7.34–7.39 (m, 4H); 7.71–7.72 (d, 1H); 8.15–8.18 (d, 1H).

Compound 9. Diisopropylamine (0.266 mL, 1.8 mmol) and 25 mL of anhydrous THF were placed under inert atmosphere. The solution was cooled to −70° C., n-butyllithium (0.72 mL, 1.8 mmol) was added via syringe and the reaction was stirred for 15 min. A solution of the thioester (0.7 g, 1.4 mmol) in 10 mL of THF was added to the reaction mixture over 10 min and the resultant dark red solution was stirred at −70° C. for 1 h. Anhydrous THF (2 mL) was added to the cold solution via addition funnel followed by pyridine (1.1 mL, 14 mmol) and POCl$_3$ (0.216 mL, 2.2 mmol) in the same manner and the mixture stirred 20 min at −70° C. The cold bath was removed and the reaction mixture was allowed to warm to room temperature. After stirring 40 min at room temperature, 2-hydroxypropionitrile (1.0 g, 14 mmol) was injected into the reaction and the reaction stirred for 3 h. The reaction was diluted with 100 mL of ethyl acetate and washed with Type I water (3×80 mL). The organic layer was dried over Na$_2$SO$_4$ and concentrated to afford 700 mg of a thick liquid. Purification of 70 mg of the crude product by prep. TLC (eluted with 70% ethyl acetate/hexanes) gave 15 mg of pure product. $^1$H NMR (CDCl$_3$): δ 1.39 (s, 9H); 2.74–2.78 (t, 4H); 4.28–4.36 (m, 4H); 4.53–4.55 (d, 2H); 7.23–7.24 (d, 1H); 7.32–7.35 (d, 2H); 7.43–7.46 (d, 2H); 7.67–7.68 (d, 1H); 8.12–8.15 (d, 1H).

Compound 3. Compound 9 is converted to compound 3 by alkaline hydrolysis of the pivalate and cyanoethyl protecting groups using the procedure of Example 3.

Example 8 Synthesis of Compound 10

Carbonyldiimidazole (2.1 g, 13 mmol) was added to a mixture of 2-(6-pivaloyloxy-2-benzothiazolyl)-5,5-dimethyl-Δ$^2$-thiazoline-4-carboxylic acid (5.0 g, 13 mmol) in 100 mL of CH$_3$CN. Thiophenol (1.54 g, 14 mmol) was added and the solution stirred for 1 h. The reaction mixture was filtered and the filtrate cooled to 4° C. to crystallize the thioester product. The product was washed with hexane and dried yielding 3.8 g of the product. $^1$H NMR (CDCl$_3$): δ 1.40 (s, 9H); 1.58 (s, 3H); 1.85 (s, 3H); 4.94 (s, 1H); 7.24–7.28 (m, 1H); 7.45 (m, 5H); 7.70–7.71 (d, 1H); 8.13–8.16 (d, 1H).

Compound 10. Diisopropylamine 1.35 mL (9.4 mmol) in 50 mL of dry THF was placed under inert atmosphere. The solution was cooled to −78° C., and n-butyllithium (3.76 mL, 9.4 mmol) was added via syringe. After 20 min, a solution of the thioester (3.5 g, 7.2 mmol) in 50 mL of THF was added to the reaction mixture dropwise. The dark red solution was stirred at −78° C. for 1 h. A solution of pyridine (5.6 g, 72 mmol) and POCl$_3$ (1.1 mL, 11 mmol) in dry THF was added dropwise and the mixture stirred for 15 min at −78° C. and then at room temperature for 1 h. 2-Hydroxypropionitrile (5.1 g, 72 mmol) was injected into the reaction and stirred continued over night at room temperature. The mixture was the concentrated under reduced pressure and the residue was taken up in 200 mL of ethyl acetate and washed with water (3×30 mL). The organic layer was dried and concentrated and the crude product was chromatographed on a column of silica gel. Isomer 1 (900 mg) and isomer 2 (1.1 g) were isolated.

Isomer 1: $^1$H NMR (CDCl$_3$): δ 1.38 (s, 9H); 2.02 (s, 6H); 2.68–2.72 (t, 4H); 4.25–4.35 (m, 4H); 7.25–7.47 (m, 6H); 7.69–7.70 (d, 1H); 8.11–8.14 (d, 1H). $^{31}$P NMR (CDCl$_3$): −10.21 to −9.94 (m).

Isomer 2: $^1$H NMR (CD$_3$COCD$_3$): δ 1.38 (s, 9H); 1.98 (s, 6H); 2.66–2.72 (m, 4H); 4.20–4.40 (m, 4H); 7.20–7.47 (m, 6H); 7.63–7.64 (d, 1H); 8.07–8.10 (d, 1H). $^{31}$P NMR (CDCl$_3$): −9.76 to −9.49 (m).

Compound 10 was converted to compound 4 by alkaline hydrolysis of the pivalate and cyanoethyl protecting groups using the procedure of Example 4.

Example 9

Reagent compositions comprising 0.1 M 221 buffer (221= 2-methyl-2-amino-1-propanol), at the pH values indicated in Table 1, 0.33 mM lucigenin, 0.1% Tween 20 and 0.66 mM compound 4 (isomer 2) were tested for production of chemiluminescence by reacting triplicate 100 μL aliquots with 10 μL of solutions of AP in water containing 0.8 fmol of enzyme at room temperature. Light production ensued upon mixing and was measured after 26 min.

TABLE 1

| pH | Background Intensity | Signal Intensity | Signal/ Background |
| --- | --- | --- | --- |
| 9.00 | 1.46 | 126.7 | 86.8 |
| 9.25 | 2.63 | 279.5 | 106.3 |
| 9.50 | 3.42 | 316.3 | 92.5 |
| 9.61 | 3.38 | 293.7 | 86.9 |
| 9.75 | 4.89 | 301.2 | 61.6 |
| 10.00 | 6.99 | 137.0 | 19.6 |

Example 10

Reagent compositions were prepared in accordance with the previous example each having a pH of 9.6 but varying concentrations of 221 buffer. Light production was tested in the same manner. Chemiluminescence was easily detected in all buffer systems in the range 0.05 M to 0.75 M 221 buffer. Light intensity was maximal with buffer concentration in the range 0.05–0.2 M.

Example 11

Reagent compositions were prepared in accordance with Example 9 each having 0.1 M 221 buffer, pH 9.6 but varying concentrations of compound 4, isomer 2. Light production was tested in the same manner. High levels of chemiluminescence resulted in all samples containing compound 4 in the concentration range 0.066 mM–0.66 mM.

Example 12

Reagent compositions were prepared in accordance with Example 9 each having 0.1 M 221 buffer, pH 9.6, 0.33 mM compound 4, isomer 2 but varying concentrations of lucigenin. Light production was tested in the same manner. High levels of chemiluminescence resulted in all samples containing lucigenin in the concentration range 0.033 mM–0.66 mM.

Example 13

Reagent compositions were prepared in accordance with Example 9 each having 0.1 M 221 buffer, pH 9.6, 0.33 mM compound 4, isomer 2, and 0.1 mM lucigenin. Various surfactants were added to the test compositions and the peak chemiluminescence produced on reaction with 8 fmol of AP was determined. Useful increases in light intensity were found when using Tween 20, Tween 40, Tween 80, Brij 35 and poly(vinylbenzyltributylphosphonium) chloride.

Example 14

Reagent compositions were prepared in accordance with Example 9 each having 0.1 M 221 buffer, pH 9.6, 0.33 mM compound 4, isomer 2 and 0.1 mM lucigenin but varying concentrations of Tween 20. Of the compositions tested, signal/background ratios were highest with Tween concentration in the range 0.03%–0.1%.

Example 15

Reagent compositions were prepared in accordance with Example 9 each having 0.1 M 221 buffer, pH 9.6, 0.33 mM compound 4, isomer 2 and 0.1% Tween 20. In place of lucigenin, Methylene Blue or Basic Blue 66 was added. Useful increases in light intensity and signal/background were found when using Methylene Blue or Basic Blue 66.

Example 16

Reagent compositions comprising 0.1 M 221 buffer, pH 9.6, 0.1 mM lucigenin, 0.1% Tween 20 and 0.33 mM compound 6 (isomer 1 or 2) were tested for production of chemiluminescence by reacting 100 µL aliquots with 10 µL of solutions of AP in water containing 8 fmol of enzyme at 25° C. Peak light intensity/background ratios were: isomer 1: 943 and isomer 2: 1800.

Example 17

Alkaline phosphatase detection sensitivity was assessed by reacting triplicate 100 µL portions of a reagent composition comprising 0.1 M 221 buffer, pH 9.6, 0.33 mM compound 4, isomer 2, and 0.1% Tween 20 and 0.1 mM lucigenin with 10 µL solutions of AP containing from $8 \times 10^{-16}$ to $8 \times 10^{-22}$ moles of enzyme. Light production at room temperature was measured at 10 min. The relation between chemiluminescence intensity and amount of enzyme is shown in FIG. 1.

Example 18

Figure 2:
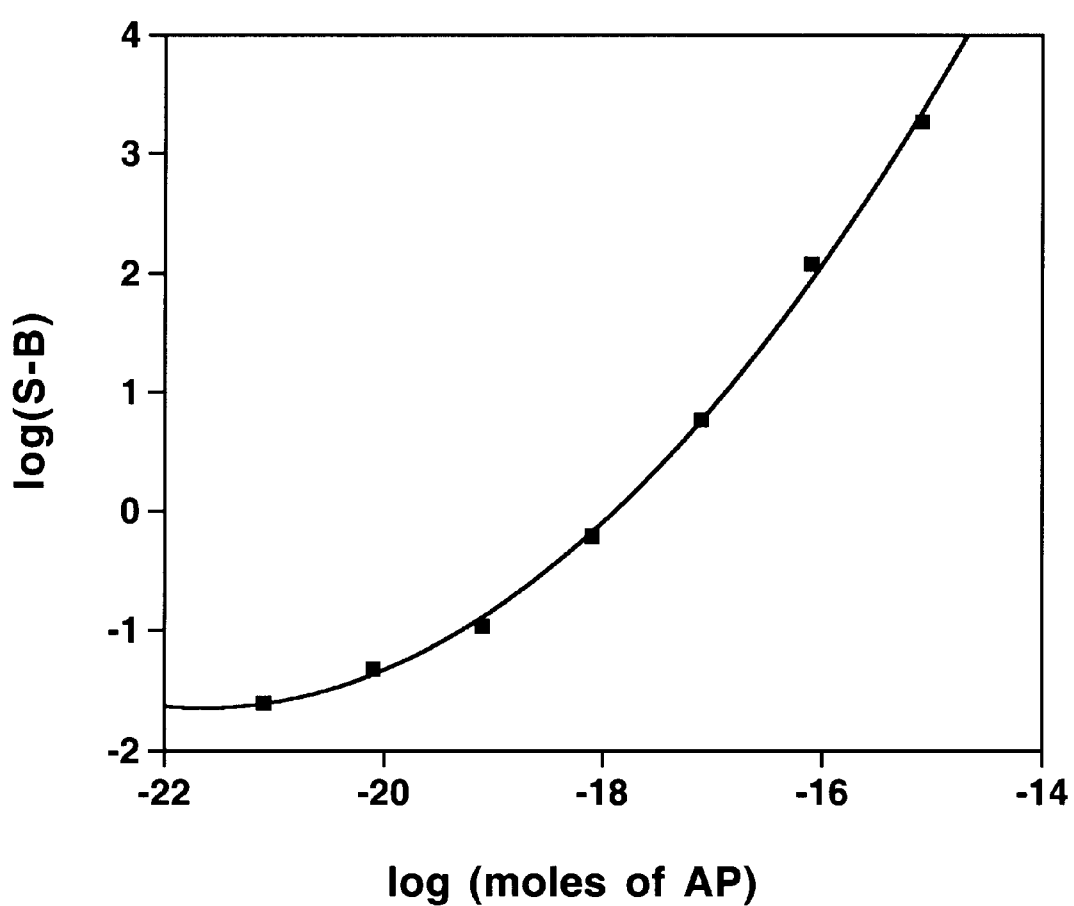
FIG. 2 is a graph relating the amount of AP to the chemiluminescence intensity emitted by a reagent of the present invention containing compound 4. Alkaline phosphatase detection sensitivity was assessed by combining 100 µL portions of a reagent composition comprising 0.1 M 221 buffer, pH 9.6, 0.33 mM compound 4, 0.1% Tween 20 and 0.64 mM Basic Blue 66 with 10 µL solutions of AP containing from $8 \times 10^{-16}$ to $8 \times 10^{-22}$ moles of enzyme. Light production at 25° C. was measured at 25 min. Data points are the average of triplicate analyses.

AP detection sensitivity was assessed by reacting triplicate 100 µL portions of a reagent composition comprising 0.1 M 221 buffer, pH 9.6, 0.33 mM compound 4, isomer 2, and 0.1% Tween 20 and 0.064 mM Basic Blue 66 with 10 µL solutions of AP containing from $8 \times 10^{-16}$ to $8 \times 10^{-22}$ moles of enzyme. Light production at room temperature was measured at 25 min. The relation between chemiluminescence intensity and amount of enzyme is shown in FIG. 2.

Example 19

Figure 3:
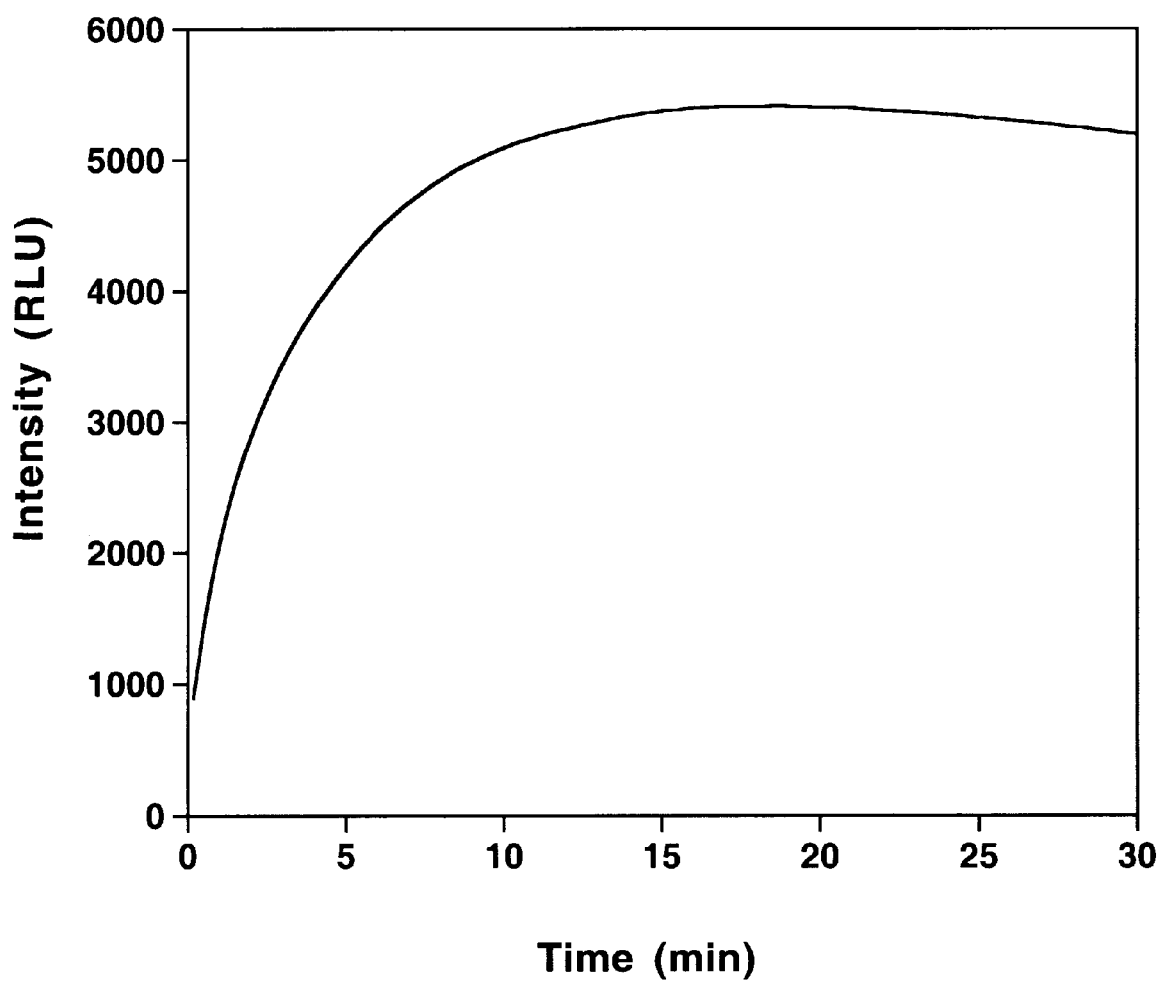
FIG. 3 is a graph showing the time profile of chemiluminescence resulting from reaction of 1.4 fmol of AP at 25° C. with 100 µL of the reagent containing compound 4, isomer 2 described in Example 19.

The chemiluminescence profile of compound 4 (isomer 2) reacted with AP is depicted in FIG. 3. Reaction of 100 µL of the reagent composition of Example 17 with $4 \times 10^{-17}$ mol of AP at 25° C. caused an instant rise in light emission which achieved maximum intensity in ca. 5 min.

Example 20

Comparisons of the intensity of chemiluminescence between the double bond isomers of compounds 4 and 5 were made. Reagent compositions were prepared by combining equal volumes of a first solution containing 0.1 M tris buffer, pH 8.8 and 0.66 mM of one isomer of compound 4 or 5, and a second solution containing 0.2 M 221 buffer, pH 9.6, 0.66 mM lucigenin and 0.5% Tween 20. A 100 µL portion of each reagent prepared in this manner was reacted at room temperature with 1 µL of a solution containing 0.8 fmol of AP. Peak light intensities in arbitrary units are shown below.

TABLE 2

| Compound | Isomer | Signal Intensity |
|----------|--------|------------------|
| 4 | 1 | 1000 |
| 4 | 2 | 2600 |
| 5 | 1 | 800 |
| 5 | 2 | 800 |

On the basis of NOE NMR experiments on the two isomers of compound 13, the synthetic precursors of the isomers of compound 4, it is believed that isomer 1 of compound 4 is the E isomer and isomer 2 is the Z isomer. The same stereochemical assignment is believed to hold for compound 5. The two isomers of 4 showed the same kinetic profile for light emission on reaction with AP. Likewise the two isomers of 5 showed the same kinetic profile for light emission on reaction with AP.

Example 30 Chemiluminescent Immunoassay of TSH

A method for detection of TSH by chemiluminescent immunoassay was performed on an IMMULITE Automated Analyzer using an IMHULITE TSH Third Generation TSH Assay kit from Diagnostic Products Corp. according to the manufacturer's protocol. The reagent of Example 17 was substituted for the detection reagent supplied in the kit.

TABLE 3

TSH Assay

| µIU/mL TSH | Intensity (CPS) |
|------------|-----------------|
| 67.3 | 13682515 |
| 10 | 3240041 |
| 1 | 189588 |
| 0.3 | 67436 |
| 0.1 | 28645 |
| 0.03 | 19519 |
| 0.01 | 16277 |
| 0.003 | 15416 |
| 0.001 | 14977 |
| Blank | 14941 |

Figure 4:
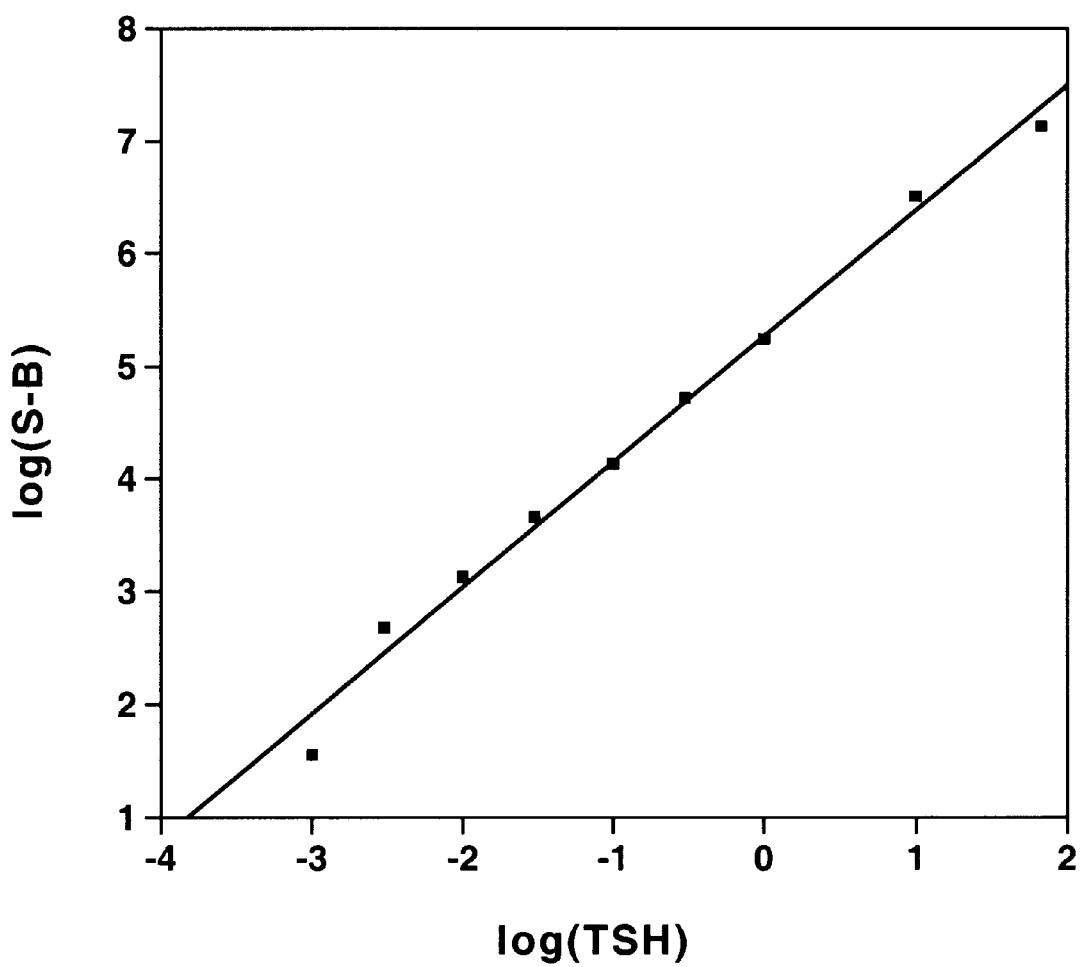
FIG. 4 is a graph showing the results of a chemiluminescent immunoassay for thyroid stimulating hormone (TSH) using a detection reagent of the invention.

The assay results as shown in FIG. 4 and Table 3 demonstrate the utility of the present compositions in providing a highly sensitive assay.

Example 33 Western Blot Assay.

Compositions of the present invention were used to detect and quantify a protein, β-galactosidase, in a Western blot with an AP-labeled antibody on polyvinylidene difluoride (PVDF) and nitrocellulose membranes. Dilutions of β-galactosidase containing from 5000, 1000, 180, 30 and 5 pg, respectively, of protein were electrophoresed at 130 V and transferred at 100 V for 23 min to PVDF (Millipore, Bedford, Mass.) and nitrocellulose (Amersham) membranes. The membranes were blocked with 1% non-fat milk and then reacted sequentially with mouse anti-β-galactosidase and sheep anti-mouse-AP conjugate. The membranes were soaked briefly with Reagent A of the present invention prepared by combining equal volumes of 0.2 M 221 buffer, pH 9.6 containing 0.5% Tween 20, 0.66 mM lucigenin and 0.1 M tris buffer, pH 8.8 containing, 0.66 mM compound 4 (isomer 2), (final pH=9.35). The membranes were placed between transparent plastic sheets and imaged with a CCD camera system for varying lengths of time. For comparison, blots were prepared in the same manner and imaged using (Reagent B) which is the reagent Lumigen™ APS-5 (Lumigen, Southfield, Mich.) which contains the compound 9-[(4-chlorophenylthio) phosphoryloxymethylene]-10-methyl-acridan, disodium salt (Reference compound 1) which has the structure shown below.

Reference compound 1

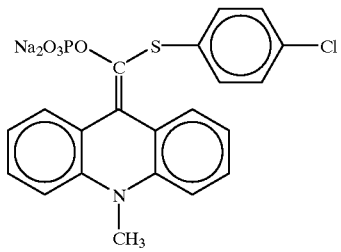

Figure 5:
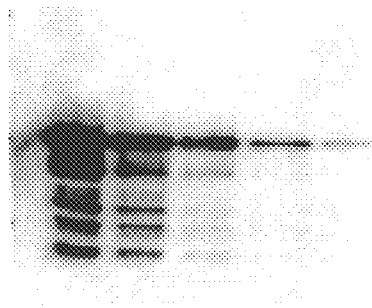
FIG. 5 is a set of CCD camera images from a Western blot assay of β-galactosidase using an AP-labeled antibody on PVDF and nitrocellulose membranes with chemiluminescent reagent compositions. Dilutions of β-galactosidase containing from 5000, 1000, 180, 30 and 5 pg, respectively, of protein were detected with a reagent of the invention and with a reagent containing an acridan phosphate.
Figure 5:
Figure 5:
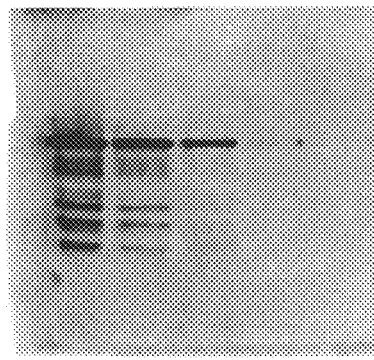
Figure 5:

Using the reagent of the present invention, the bands for β-galactosidase were detected immediately after wetting the membranes with Reagent A on both PVDF and nitrocellulose membranes using a 1 min exposure as shown in FIG. 5. Equivalent exposures obtained with Reagent B produced much less intense images than Reagent A on both membranes.

Example 34

A dot blot assay of digoxigenin-labeled DNA (pBR328) was performed using detection reagents (Reagents A and C) prepared in accordance with the present invention. Reagent A is described the previous example. Reagent C was formulated identically with Reagent A but contained isomer 1 of compound 4 instead of isomer 2.

Positively charged nylon membrane, antibody-AP conjugate, labeled DNA and blocking agent were obtained from Boehringer-Mannheim. The wash buffer was 0.1 M maleic acid, pH 7.5, 0.15 M NaCl.

Figure 6:
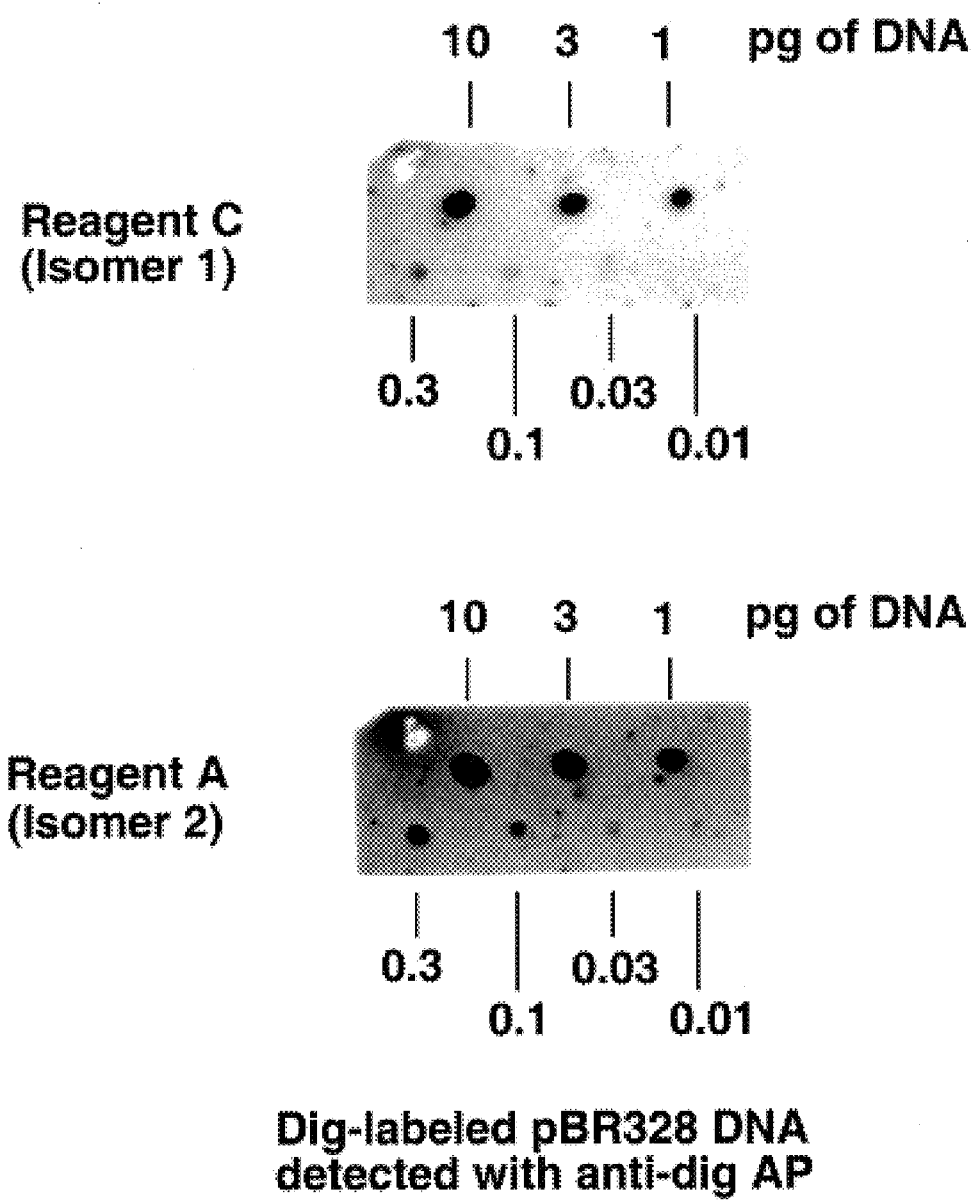
FIG. 6 is a set of CCD camera images from a dot blot assay of digoxigenin-labeled pBR328 DNA using an AP-labeled antibody.

DNA dilutions (10, 3, 1, 0.3, 0.1, 0.03, 0.01 pg) were dot blotted onto nylon membranes. Blots were soaked in maleic acid wash buffer for 3 min and then blocked using 2% blocking buffer. The blots were soaked in anti digoxigenin-AP conjugate, washed in maleic acid buffer containing 0.3% Tween 20 and then soaked for 3 min in 0.1 M tris, pH 9.5 containing 0.1 M NaCl. Excess buffer was drained off and blots soaked in detection reagents A or C. Excess reagent was drained off, the blots placed between transparent sheets and imaged with a CCD camera system for varying lengths of time. An immediate 1 min exposure detected the 10 pg–0.03 pg spots with both reagents. After 30 min, all seven spots were detected with a 1 min exposure (FIG. 6). Multiple exposures could be performed for at least a day.

Example 35

Figure 7:
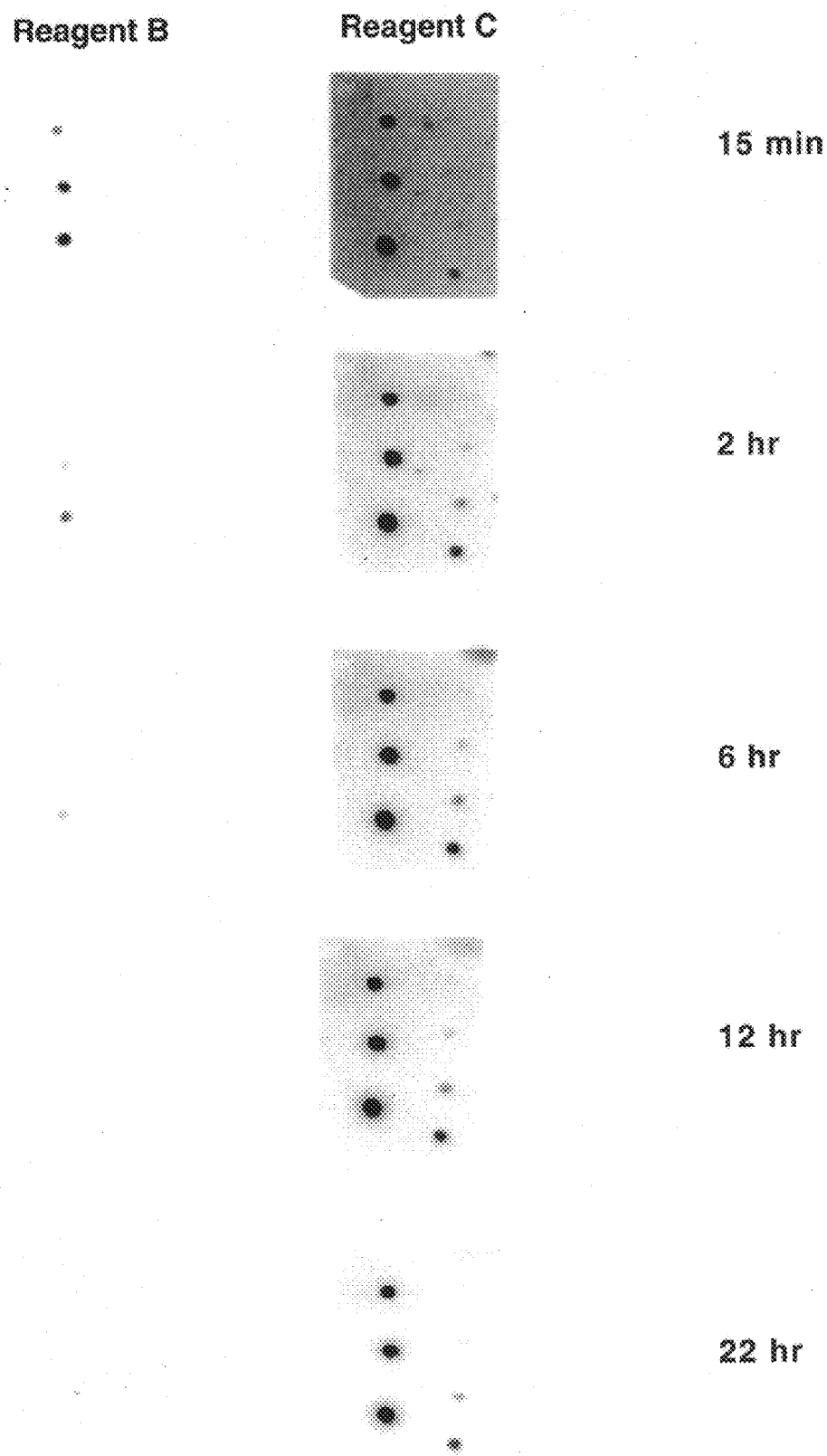
FIG. 7 is a set of CCD camera images from a dot blot assay of digoxigenin-labeled pBR328 DNA using an AP-labeled antibody.

A dot blot assay was conducted as described in Example 34 using as detection reagents Reagent C and Reagent B described in the preceding examples. Reagent C produced significantly higher light intensities measured by the CCD camera than Reagent B (FIG. 7). Light emission from the blot developed with Reagent C persisted for many hours after emission had decayed from the blot developed with Reagent B.

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A reagent composition which comprises in an aqueous solution:

a) at least one of:

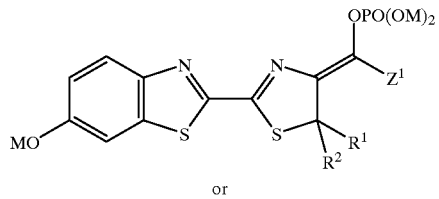

or

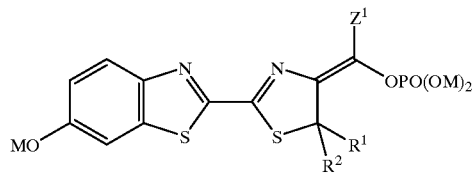

wherein $Z^1$ is a group selected from $OR^3$ and $SR^3$ and $R^3$ is selected from substituted or unsubstituted alkyl, substituted or unsubstituted aryl, and substituted or unsubstituted aralkyl groups, $R^1$ and $R^2$ are independently selected from substituted or unsubstituted alkyl and which can be combined as a cycloalkyl group, substituted or unsubstituted aryl, and substituted or unsubstituted aralkyl, and M is selected from H and a cationic center; and b) a cationic aromatic compound.

2. The composition of claim 1 wherein the cationic aromatic compound is selected from lucigenin, Basic Blue 41, Basic Blue 66 and Methylene Blue.

3. The composition of claim 2 further comprising a nonionic surfactant.

4. The composition of claim 3 wherein the nonionic surfactant is selected from polyoxyethylenated alkylphenols, polyoxyethylenated alcohols, polyoxyethylenated ethers and polyoxyethylenated sorbitol esters.

5. The composition of claim 1 wherein $R^1$ and $R^2$ are each an alkyl group.

6. The composition of claim 5 wherein $Z^1$ is selected from O—Ar and S—Ar groups wherein Ar is a substituted or unsubstituted aryl group.

7. The composition of claim 6 wherein Ar is selected from phenyl, substituted phenyl and naphthyl.

8. The composition of claim 5 wherein $Z^1$ is an S—Ar group, $R^1$ and $R^2$ are each methyl, and M is selected from H and alkali metal ions.

9. The composition of claim 8 wherein the compound of formula I has the formula:

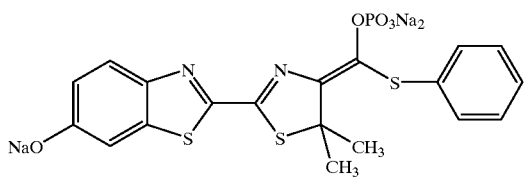

or

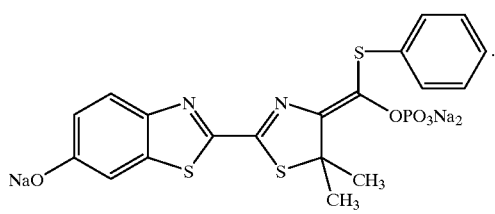

10. The composition of claim 8 wherein the compound of formula I has the formula:

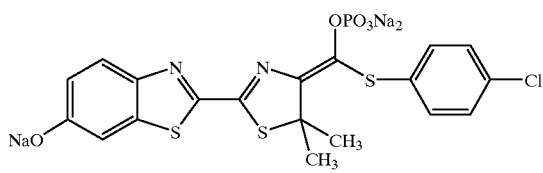

or

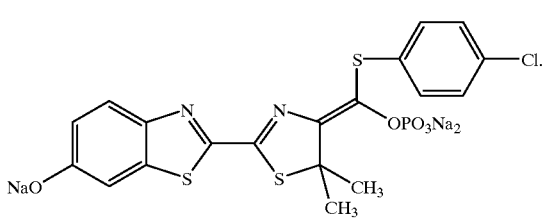

11. The composition of claim 8 wherein the compound of formula I has the formula:

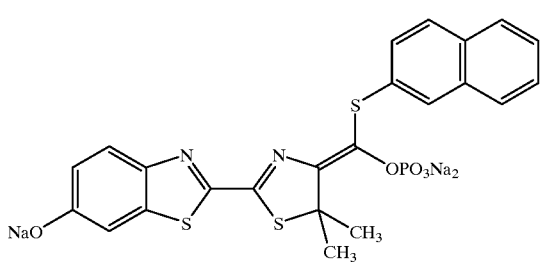

or

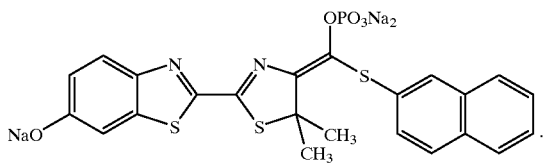

12. A method for producing chemiluminescence which comprises reacting a phosphatase enzyme with a compound having the formula:

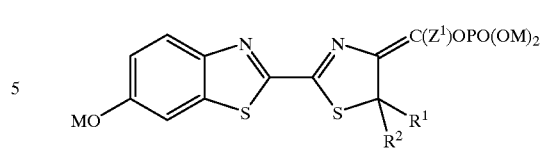

wherein $Z^1$ is a group selected from $OR^3$ and $SR^3$ and $R^3$ is selected from substituted or unsubstituted alkyl, substituted or unsubstituted aryl, and substituted or unsubstituted aralkyl groups, $R^1$ and $R^2$ are independently selected from substituted or unsubstituted alkyl and which can be combined as a cycloalkyl group, substituted or unsubstituted aryl, and substituted or unsubstituted aralkyl, and M is selected from H and a cationic center.

13. The method of claim 12 wherein the phosphatase enzyme is selected from the group consisting of bacterial alkaline phosphatase, mammalian alkaline phosphatase, plant acid phosphatase, mammalian acid phosphatase and alkaline phosphatase conjugates.

14. The method of claim 12 wherein the phosphatase enzyme is an alkaline phosphatase.

15. The method of claim 13 wherein the alkaline phosphatase conjugate comprises alkaline phosphatase conjugated to a biological molecule selected from the group consisting of haptens, antibodies, proteins, nucleic acids and oligonucleotides.

16. A method for detecting an analyte in a sample by a chemiluminescent assay procedure which comprises:
(a) contacting the sample with at least one compound of formula I and, if not present in the sample, a phosphatase enzyme to produce chemiluminescence,

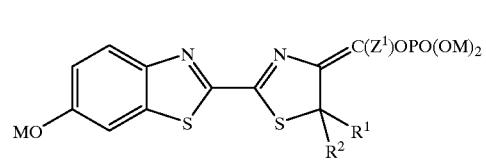

wherein $Z^1$ is a group selected from $OR^3$ and $SR^3$ and $R^3$ is selected from substituted or unsubstituted alkyl, substituted or unsubstituted aryl, and substituted or unsubstituted aralkyl groups, $R^1$ and $R^2$ are independently selected from substituted or unsubstituted alkyl and which can be combined as a cycloalkyl group, substituted or unsubstituted aryl, and substituted or unsubstituted aralkyl, and M is selected from H and a cationic center;
(b) detecting the chemiluminescence; and
(c) relating the amount of the chemiluminescence to the amount of the analyte in the sample.

17. The method of claim 16 wherein the analyte to be detected is the phosphatase enzyme.

18. The method of claim 16 wherein the analyte to be detected is an inhibitor of the enzyme.

19. The method of claim 16 further comprising reacting the analyte in the sample with an analyte binding compound which specifically binds with the analyte wherein the analyte-binding compound is conjugated with alkaline phosphatase.

20. The method of claim 19 wherein the analyte-binding compound is selected from the group consisting of haptens, antibodies, proteins, nucleic acids and oligonucleotides.

21. The method of claim 16 wherein the phosphatase enzyme is directly attached to the analyte as a label.

22. The method of claim 16 further comprising reacting the analyte in the sample with an analyte binding compound and a phosphatase-conjugated specific binding substance for the analyte binding compound.

23. The method of claim 16 further comprising reacting the analyte in the sample with:

(a) a labeled analyte binding compound comprising an analyte binding compound which specifically binds with the analyte and at least one second specific binding substance; and (b) a phosphatase-labeled binding partner for the second specific binding substance.

24. The method of claim 16 wherein the detection is performed on a membrane.

25. The method of claim 16 further comprising providing the compound of formula I in a reagent composition comprising, in an aqueous solution, the compound of formula I and a cationic aromatic compound.

26. The method of claim 16 wherein the chemiluminescence is detected by a charge-coupled device or a red-sensitive photodiode.

* * * * *